(12) United States Patent
Jarrell

(10) Patent No.: US 7,976,481 B2
(45) Date of Patent: Jul. 12, 2011

(54) APPARATUS FOR DETECTING ENDOMETRIOSIS

(76) Inventor: John F. Jarrell, Alberta (CA)

( * ) Notice: Subject to any disclaimer, the term of this patent is extended or adjusted under 35 U.S.C. 154(b) by 170 days.

(21) Appl. No.: 12/253,771

(22) Filed: Oct. 17, 2008

(65) Prior Publication Data

US 2009/0043174 A1 Feb. 12, 2009

Related U.S. Application Data

(62) Division of application No. 11/074,856, filed on Mar. 8, 2005, now Pat. No. 7,462,157.

(60) Provisional application No. 60/553,055, filed on Mar. 15, 2004.

(51) Int. Cl.
*A61B 5/103* (2006.01)
(52) U.S. Cl. ............... 600/591; 128/899; 600/300
(58) Field of Classification Search ........... 600/423, 600/554, 591
See application file for complete search history.

(56) References Cited

U.S. PATENT DOCUMENTS

| | | | |
|---|---|---|---|
| 2,321,355 A * | 6/1943 | Berman ............... 600/11 |
| 2,393,717 A | 1/1946 | Speaker | |
| 3,749,089 A | 7/1973 | Derr | |
| 4,572,162 A | 2/1986 | Livesay et al. | |
| 5,458,142 A | 10/1995 | Farmer et al. | |
| 5,769,791 A | 6/1998 | Benaron et al. | |
| 5,800,350 A | 9/1998 | Coppleson et al. | |
| 5,973,595 A | 10/1999 | Scrivner et al. | |
| 6,080,118 A | 6/2000 | Blythe | |
| 6,549,800 B1 | 4/2003 | Atalar et al. | |

OTHER PUBLICATIONS

Iizuka et al, Chemical Assay of Iron in Ovarian Cysts: A New Diagnostic Method to Evaluate Endometriotic Cysts, Gynecol Obset Invest., 1998, 46(1), pp. 58-60.
Gandon, Yves, "Iron, liver, and MRI", Jun. 10, 2001. University of Rennes, p. 1-3.
Falcone et al., The Elusive Diagnostic Test for Endometriosis. American Society for Reproductive Medicine, Fertility and Sterility, Oct. 2003, pp. 886-888, vol. 80, No. 4, Elsevier Inc., U.S.A.
Gagne et al., Development of a nonsurgical diagnostic tool for endometriosis based on the detection of endometrial leukocyte subsets and serum CA-125 levels, American Society for Reproductive Medicine, Fertility and Sterility, Oct. 2003, pp. 876-885, vol. 80, No. 4, Elsevier Inc. U.S.A.
Van Langendonckt, et al., Iron overload in the peritoneal cavity of women and pelvic endometriosis, American Society for Reproductive Medicine, Fertility and Sterility, Oct. 2002, pp. 712-718, vol. 78, No. 4, Elsevier Science Inc., U.S.A.

(Continued)

*Primary Examiner* — Max Hindenburg
*Assistant Examiner* — Renee Danega
(74) *Attorney, Agent, or Firm* — Scott T. Griggs; Griggs Bergen LLP

(57) ABSTRACT

A vaginal probe includes a metal detection sensor for detecting the presence of ferrous-laden endometriotic tissues. The probe is electrically connected to external electronic circuitry for interpreting the readings taken by the sensor and for providing a qualitative or quantitative measurement of the amount of endometriotic tissues present. The probe is inserted in either the vagina or peritoneal cavity of a patient to detect the location and the relative amounts of iron or ferrous-laden tissues in the pelvic area of the patient. Using the probe and monitoring the readings over time as part of pelvic exams assists in determining the early onset or progression of endometriosis and/or the response to one or more therapies being provided to the patient to treat the disease.

3 Claims, 5 Drawing Sheets

OTHER PUBLICATIONS

Farquhar, Extracts from "Clinical Evidence"—Endometriosis, BMJ, May 27, 2000, pp. 1449-1452, vol. 320.

Fujiwara et al., Acute elevation of plasma D-dimer levels associated with rupture of an ovarian endometriotic cyst Case report, Human Reproduction, 2003, pp. 338-341, vol. 18, No. 2.

Scurry et al., Classification of Ovarian Endometriotic Cysts, International Journal of Gynecological Pathology, 2001, pp. 147-154, vol. 20, Lippincott Williams & Wilkins, Baltimore.

Fortin et al., An improved mouse model for endometriosis allows noninvasive assessment of lesion implantation and development, American Society for Reproductive Medicine, Fertility and Sterility, Sep. 2003, pp. 832-838, vol. 80, Suppl. 2, Elsevier Inc., U.S.A.

Quinn et al., Diagnosis of Endometriosis: utility of MRI?, American Society for Reproductive Medicine, Fertility and Sterility, Oct. 2003, pp. 1071-1072, vol. 80, No. 4, Elsevier Inc., U.S.A.

Bedaiwy et al., Laboratory testing for endometriosis, Clinics Chimica Acta 340, 2004, pp. 41-56, Elsevier B.V.

Maia et al., Evaluation of Ovarian Endometriotic Cysts by Transvaginal Sonography and Videolapamscopy (Abstract only), J Am Assoc Gynecol Laparosc., Aug. 1996, 4, Supplement, S27.

Takahashi et al., Magnetic resonance relaxation time in evaluating the cyst fluid characteristics of endometrioma (Abstract only), Hum Reprod., Apr. 1996, 11(4), pp. 857-860.

Moen et al., Histological confirmation of endometriosis in different peritoneal lesions (Abstract only), Acta Obstet Gynecol Scand., Jul. 1992, 71(5), pp. 337-342.

Nishi et al., Magnetic resonance imaging of the ovarian cyst: Its diagnostic value of endometrial cyst (Abstract only), Med Prog Technol., 1990, 16(4), pp. 201-212.

* cited by examiner

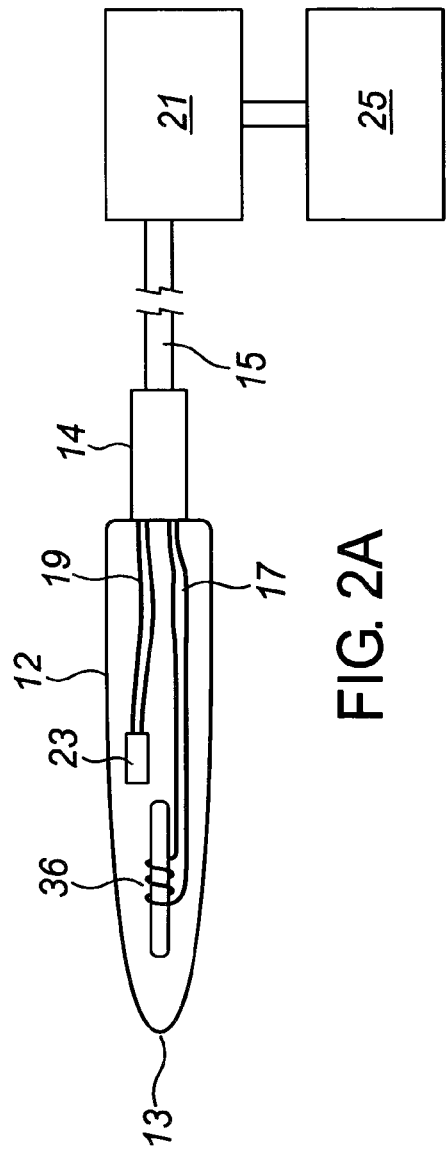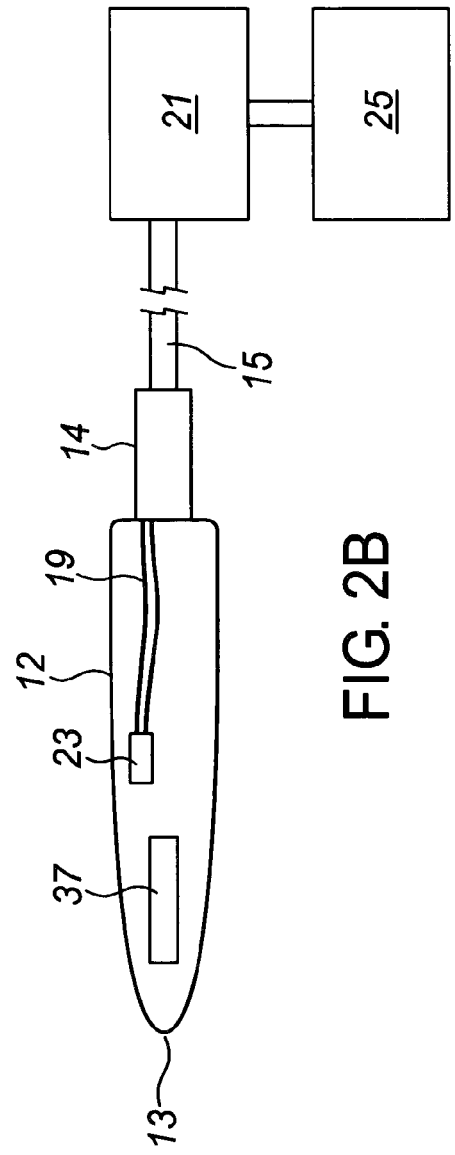

APPARATUS FOR DETECTING ENDOMETRIOSIS

CROSS REFERENCE TO RELATED APPLICATIONS

This application claims priority from U.S. Provisional Application No. 60/553,055 filed Mar. 15, 2004, entitled "Method and Apparatus for Detecting Endometriosis," and U.S. application Ser. No. 11/074,856 filed Mar. 8, 2005, entitled "Method and Apparatus for Detecting Endometriosis," now pending. These applications are incorporated herein by reference for all purposes.

BACKGROUND OF THE INVENTION

The present invention relates to the field of diagnostic methods and apparatus for detecting endometriosis in a patient. More specifically, the present invention relates to a non-surgical method and apparatus for detecting endometriosis.

Endometriosis is defined as the presence of endometrial tissue in aberrant locations of the body, usually in the pelvis.

There are no techniques for the confirmation of this disease other than the pathological assessment of the tissue that is removed or biopsied during a surgical procedure. Magnetic Resonance Imaging ("MRI") is helpful in the detection but the standard of care still requires histological confirmation. The pathological definition is based on the recognition that there are endometrial glands and endometrial stroma located in deposits of the organs involved. By definition, these tissues and organs are outside the uterine cavity. The glands and stroma have the same characteristics as those located in the uterine lining the so-called endometrium.

Notably, these tissues are also associated with hormonally-induced changes that tend to be similar to those identified in the uterus. These patterns in the uterus are called proliferative and secretary, depending on the activity of the glands in response to ovarian hormonal stimulation. During the early proliferative phase, the dominant hormonal stimulation is estradiol leading to an increasing proliferative appearance in the glands. After ovulation, the dominant pattern is secretory due to the presence of both estradiol and progesterone. It should be noted that the endometriotic tissues are not always identified as having exactly parallel histological appearances as those in the uterus.

There is an additional confounder to this situation. The surgeon making a decision to biopsy the disease does so on the basis of the visual appearance of the tissues. A variety of appearances of the endometriotic tissues are possible from a simple vesicle to highly pigmented lesions of the tissues due to the deposition of iron as hemosiderin and ferritin directly into the tissues. Often there is a discrepancy in the diagnosis because the visual appearance of the disease observed by the surgeon is not always confirmed by the pathologist. This is also present in the ovary where endometriosis can be the cause of bloody or chocolate cysts.

There are other causes of such a chocolate cyst, such as a corpus luteum cyst, or any other cyst that has undergone hemorrhagic degeneration. Non-endometriotic chocolate cysts tend to resolve over a relatively short span of time, unlike ovarian endometriomas.

Unless there is evidence of endometriosis elsewhere such as located in the vagina where it can be visualized easily during a pelvic examination (which is very unusual), the diagnosis requires a surgical procedure to be undertaken, although MRI may be helpful.

The disease is generally quite tightly associated with the reproductive life span of women. It only occurs in primates that menstruate. The disease is thought to have a major part of its origin from the implantation of endometrial tissues that have implanted on normal tissue during retrograde menstruation. Alternatively, it is thought there may be a process of metaplasia in which the cells of the particular tissue undergo metaplasia to form the endometrial glands. One single method has not explained all of the manifestations of the disease.

There is increasing interest in the disease as one of the chronic illnesses associated with both a genetic and an environmental interaction. Some putative genetic markers have been identified but the situation remains one of intense interest. The environmental aspects have included the possibility that environmental toxins can affect the immune system in such a manner that the retrograde-passed endometrial tissues are not removed by the body's usual defense mechanisms. These are most significantly associated with the exposure to dioxin in subhuman primates, although there are conflicting results in terms of severe human exposures. A more robust statement has recently been reported in the medical literature, as noted below.

Although there has been a reported increase in the incidence and prevalence of this disease, this may be an ascertainment bias given the greater appreciation of smaller, less differentiated lesions more recently and the greater impact of medical therapy for infertility and pelvic pain over the past few decades. It is theorized, however, that increased exposures to priority chemicals over the past 40 years might have an important contributory role in the disease.

Several reports have suggested that iron may be playing a role in the pathophysiology of the condition. Iron is present in the tissues and the peritoneal fluid. It can be identified through histological techniques using Prussian blue staining. Iron is also measured in the peritoneal fluid that is often present to varying degrees in the pelvis. It can be identified as iron, ferritin and transferrin in concentrations that are similar to those associated with the serum or higher.

The role that iron is playing in the disease is uncertain at present. There is hypothetically a role of the disease in the generation of tissue injury and fibrosis through the generation of adhesions through the Fenton reaction. This well known biochemical reaction uses the electron configuration of the iron atom to generate singlet oxygen in the presence of peroxide and organic molecules. It results in the degradation of these organic chemicals. However, there is controversy surrounding the activities of this theory because of the varied responses to the measurements of the products of lipid peroxidation in the peritoneal cavity.

More recent findings have implicated the tissue metallothionenes in the alteration of the normal tissue architecture. Also, there have been developments in the use of magnetic resonance imaging to detect the disease and provide an alternative to surgical therapy in the staging of the disease. It should be noted, however, that the measurement of iron in the peritoneal fluid of women should be considered an experimental procedure.

The symptoms and signs of the disease are consistent with alterations in the anatomy owing to scarring and deformities of the normal tissues. Patients with the disease are noted to have commonly experienced infertility and pelvic pain. In both cases, the actual mechanisms are not clearly understood. In some cases, the infertile subjects have minimal disease and the cause of the infertility is considered to be unknown. In more advanced cases, the disease disrupts tubal and ovarian function such that there is a physical barrier to the co-location of the egg and sperm.

Similarly, in subjects with pelvic pain, there can be severe pain and disability that can be associated with minimal amounts of endometriosis. In other more advanced cases the disease takes on a definite invasive and nodular appearance that progresses during the reproductive years until menopausal reduction in hormonal support tends to lessen the impact of the subject's experience of pain.

The actual processes of the disease are not fully understood. Thus, the direct approach to the disease is not apparent at present but is directed to the symptoms of this fundamentally mysterious condition. Approaches to the care of patients have been identified through expert panels and consensus conferences. In general, the common approach is to undertake a medical approach through the use of certain medications and turn to surgery when this is unsuccessful. It should be noted, however, the disease is very diverse in its presentation and individualization of care is important.

From a medical perspective, there is an approach to develop some degree of control over the menstrual cycle. The oral contraceptive is commonly used as it limits the amount of menstrual bleeding experienced by many women, which has a direct impact on the degree of pain experienced. Also, some feel this drug limits further deposition of implants and provides a progestogenic environment that allows the tissue to heal.

More significant progestogenic action can be achieved through the use of depot forms of progesterone. The use of GnRH agonists has been commonplace. These drugs initiate a pseudo menopause such that the ovarian production of hormones is greatly reduced to levels that would be identified at menopause. One additional drug, Danazol, is a steroid with mild androgenic actions that has also been used to suppress the disease.

These drugs and their approaches have been used in the management of both infertility and pelvic pain. Of course, in the area of infertility, there has been a move to new reproductive technologies to bypass the known or unknown factors in the pelvis and permit fertilization of the embryo.

Magnetic resonance imaging (MRI) has been used to explore the appearance of the disease using low-energy radio frequency radiation, magnetic fields and computers to create 2-D images based on the varying local environments of water molecules in the body. The appearance of endometriomas or endometriotic cysts of the ovary on MRI is variable and depends on the concentration of iron and protein in the fluid from blood degradation. Most endometriomas have a gross appearance of "chocolate cysts," representing highly concentrated blood products.

MRI demonstrates these endometriomas as cystic masses with very high signal on T1-weighted images and very low signal on T2-weighted images. This low signal intensity on the T2-weighted images is termed "shading" and occasionally occurs in a gradient from higher to lower signal intensity. This pattern of signal intensity results from the high iron concentration in the endometrioma and is rarely seen in other masses of any type.

Multiple high-signal lesions, usually in the ovaries, on T1-weighted images also are highly suggestive of endometriosis. Peritoneal implants initially are small serosal lesions and usually escape detection. Larger fibrotic implants of endometriosis are seen on MRI as spiculated nodules of very low signal intensity on T2-weighted images. These occur commonly in the cul-de-sac and less commonly on the bladder dome, rectum, umbilicus, or in pelvic surgical scars.

Dilated fallopian tubes occasionally are seen on MRI in patients with endometriosis; these demonstrate high signal intensity on T1-weighted images, indicative of bloody fluid.

MRI also can demonstrate the complications of endometriosis. Bowel obstructions and hydronephrosis occasionally can be seen. Since longer imaging times are required for MRI, anti-peristaltic medication can improve visualization of bowel. In one study, MRI showed a sensitivity of 90-92%/o and a specificity of 91-98% for the diagnosis of endometrioma in patients with adnexal masses. Thus, MRI is an accurate technique in distinguishing endometriomas from other masses. Other studies have indicated the combined use of MRI and laparoscopy are complementary and formulate the best currently available diagnostic approach.

Surgical therapy is frequently undertaken either through diagnostic or therapeutic laparoscopy or through laparotomy. With advances in the development of laparoscopic surgery, there is a decrease in the need for laparotomy but there is still a significant amount of surgery being undertaken, particularly, oophorectomy and hysterectomy. One additional concern is the fact that many subjects with the disease have repeated laparoscopy procedures that eventually culminate in a hysterectomy.

To reduce the number of laparoscopy procedures on a patient for diagnostic purposes, it is, therefore, desirable to have a non-surgical diagnostic method and apparatus for detecting the presence of endometriosis in the patient.

Contemporary findings on pelvic endometriosis have been reported in the literature as follows:

(1) Cramer D W, Missmer S A. The epidemiology of endometriosis. Ann NY Acad Sci 2002; 955:11-22.
(2) Zondervan K, Barlow D H. Epidemiology of chronic pelvic pain. Baillieres Best Pract Res Clin Obstet Gynaecol 2000; 14(3):403-414.
(3) Zondervan K T, Cardon L R, Kennedy S H. The genetic basis of endometriosis. Curr Opin Obstet Gynecol 2001; 13(3):309-314.
(4) Kennedy S. The genetics of endometriosis. Eur J Obstet Gynecol Reprod Biol 1999; 82(2):129-133.
(5) Kennedy S. Genetics of endometriosis: a review of the positional cloning approaches. Semin Reprod Med 2003; 21(2):111-118.
(6) Kennedy S. The genetics of endometriosis. J Reprod Med 1998; 43(3 Suppl):263-268.
(7) Rier S, Foster W G. Environmental dioxins and endometriosis. Sermin Reprod Med 2003; 21(2):145-154.
(8) Rier S, Foster W G. Environmental dioxins and endometriosis. Toxicol Sci 2002; 70(2):161-170.
(9) Rier S E. The potential role of exposure to environmental toxicants in the pathophysiology of endometriosis. Ann NY Acad Sci 2002; 955:201-212.
(10) Eskenazi B, Mocarelli P, Warner M, Samuels S, Vercellini P, Olive D et al. Serum dioxin concentrations and endometriosis: a cohort study in Seveso, Italy. Environ Health Perspect 2002; 110(7):629-634.
(11) Eskenazi B, Mocarelli P, Warner M, Samuels S, Vercellini P, Olive D et al. Seveso Women's Health Study: a study of the effects of 2,3,7,8-tetrachlorodibenzo-p-dioxin on reproductive health. Chemosphere 2000; 40(9-11):1247-1253.
(12) Guo S W. The Link between Exposure to Dioxin and Endometriosis: A Critical Reappraisal of Primate Data. Gynecol Obstet Invest 2004; 57(3):157-173.
(13) Van Langendonckt A, Casanas-Roux F, Donnez J. Oxidative stress and peritoneal endometriosis. Fertil Steril 2002; 77(5):861-870.

(14) Van Langendonckt A, Casanas-Roux F. Donnez J. Iron overload in the peritoneal cavity of women with pelvic endometriosis. Fertil Steril 2002; 78(4):712-718.

(15) Polak G, Rola R, Gogacz M, Koziol-Montewka M, Kotarski J. Malonyldialdehyde and total antioxidant status in the peritoneal fluid of infertile women. Ginekol Pol 1999; 70(3):135-140.

(16) Osteen K G, Yeaman G R, Bruner-Tran K L. Matrix metalloproteinases and endometriosis. Semin Reprod Med 2003; 21(2):155-164.

(17) Osteen K G, Bruner-Tran K L, Keller N R, Eisenberg E. Progesterone-mediated endometrial maturation limits matrix metalloproteinase (MMP) expression in an inflammatory-like environment: a regulatory system altered in endometriosis. Ann NY Acad Sci 2002; 955:37-47.

(18) Zanardi R, Del Frate C, Zuiani C, Bazzocchi M. Staging of pelvic endometriosis based on MRI findings versus laparoscopic classification according to the American Fertility Society. Abdom Imaging 2003; 28(5):733-742.

(19) Olive D L, Pritts E A. The treatment of endometriosis: a review of the evidence. Ann NY Acad Sci 2002; 955:360-372.

(20) Martin D C. Research aspects of endometriosis surgery. Ann NY Acad Sci 2002; 955:353-359.

(21) Togashi, K.; Nishimura, K.; Kimura, I.; Tsuda, Y.; Yamashita, K.; Shibata, T.; Nakano, Y.; Konishi, J.; Konishi, I.; Morin T. Endometrial cysts: diagnosis with MR imaging. Radiology 180:73-78.

BRIEF SUMMARY OF THE INVENTION

The present invention provides method and apparatus for detecting endometriosis in a patient. The present invention is based on the insight that there is identifiable iron located in the tissues of women who suffer from endometriosis. The apparatus of the present invention is used by a clinician examining a patient during a pelvic examination or during surgical exploration and permits the diagnosis of endometriosis through the detection of endometriotic tissues.

Iron is not normally identified in a concentrated fashion in the human pelvis. Although iron is a normal constituent of human blood, it does not usually become aggregated in the tissues of the pelvis. In the medical condition known as endometriosis, iron collects in the pelvis in the areas affected by the disease. Endometriosis is defined as the abnormal localization of endometrial tissue in sites other than the uterine lining.

The most frequent locations of these implants are the uterosacral ligaments, the ovaries and the ovarian fossae. Implants have the capacity to grow and become fibrotic. The iron is localized in these areas of pathology and collected as hemosiderin or ferritin. The iron remains in the area for long periods and does not enter the redistributing pools of iron identified for the iron in red blood cells. The iron is readily identifiable in biopsies through histological staining methods using Prussian blue stains.

The amounts of iron appear to correlate roughly with the extent of endometriosis although this is empiric and has not been subjected to a specific analysis owing to the difficulties associated with such research. The amounts of endometriosis are highly individualized among the populations of patients with this condition. The extent of the amount of implanted tissues and iron is dependent upon the stage of the disease, the age of the patient, the medical and surgical treatments received.

The present invention takes advantage of the ferromagnetic properties of iron and detects the presence of endometriosis by providing a probe having metal detection means to locate endometriotic tissues in the patient.

The apparatus of the present invention is a probe having a distal end enclosing metal detection means. In one embodiment, the detection means is a coil located within the distal end with the coil energized by a bias current provided by an excitation source or oscillator. A coil energized by a current generates a magnetic field emanating from the core of the coil. When the coil is moved toward ferrous materials, the coil's magnetic field will be disrupted by the presence of the ferrous material. This disruption in the magnetic field will cause fluctuations in the current flowing through the coil. The change in the current is a function of how close the coil is to the ferrous material and the amount and shape of the ferrous material present.

One skilled in the art will appreciate that a biased or energized coil is but one means for detecting the presence of ferrous materials and that other sensing devices may be similarly used in place of a coil disposed in the distal end of a probe. An alternate technology that may be used is to provide a sensor disposed in the probe that generates a magnetic field which is monitored by a Hall effect device also disposed in the probe. The magnetic field may be generated by any suitable means such as an energized coil or a permanent magnet, as possible examples. When the probe is moved toward the ferrous-laden or endometriotic tissues, these tissues will cause fluctuations in the magnetic field that can be detected by the Hall effect device.

The Hall effect device can be placed in a circuit to control a voltage potential or the flow of a current in the circuit. Changes in the magnetic field detected by the Hall effect device translate into changes in the voltage or current in the circuit that can be detected and interpreted by circuit means operatively connected to the detection means.

The circuit means measures the current or voltage emanating from the detection means and any disruptions thereto caused by the presence of ferrous materials, such as endometriotic tissues, in close proximity to the detection means. Those skilled in the art will appreciate that the circuit means may be embodied in analog circuitry, either as discrete or integrated electronic components, or in digital circuitry incorporating an analog-to-digital converter for receiving the current or voltage produced by the detection means for processing by a microprocessor or a digital signal processor. The circuit means, regardless of its embodiment, detects the changes in the current or voltage produced by the detection means and interprets the current or voltage changes as either qualitative or quantitative measurements of the ferrous-laden tissue present in the patient.

Indicator means are operatively connected to the circuit means and provide a visual indication of the current or voltage emanating from the detection means and, what is more important, any disruptions in the current or voltage thereto thereby indicating that the probe is in the presence of ferrous-laden or endometriotic tissues. The indicator means may take the form of a current or voltage meter whereby deflections in the meter's needle indicate fluctuations in the current or voltage. Alternatively, the indicator may take the form of an electronic display providing information in alphanumeric characters as to the absolute value of the current or voltage and/or changes in the nominal current or voltage emanating from the detection means.

The method of the present invention comprises the use of the apparatus as a non-surgical in vivo diagnostic technique to detect the presence of endometriosis. The probe is placed in the vagina of the patient and then moved within the patient to determine if any endometriotic tissues can be detected. The apparatus can be configured to provide either a qualitative or quantitative measurement. In other words, the apparatus may be used to measure the absolute amount of ferrous material detected or to determine a reading that is then compared to a benchmark or base line reading.

As this method is non-surgical in nature, a number of diagnostic treatments using the present invention can be made on a patient without the high costs and limited access of MRI or the dangers or risks caused by multiple laparotomy or laparoscopy procedures. Accordingly, the present invention can be used as part of regular examinations to detect the early onset of endometriosis in a patient. The present invention can also be used at regular intervals while the patient is undergoing medical treatment for endometriosis to determine the efficacy of the treatment.

The present invention may also be used in surgical procedures, such as laparotomies or laparoscopies, to locate ferrous-laden or endometriotic tissues in the peritoneal cavity of the patient.

Broadly stated, the present invention provides a method for detecting endometriosis, the method comprising the steps of providing a probe, suitable for in vivo use and having detection means for detecting the presence of ferrous-laden tissue, and placing the probe in the vagina or peritoneal cavity of the patient; moving the probe in the vagina or peritoneal cavity of said patient until the probe detects the presence of ferrous-laden tissue; and measuring the amount of ferrous-laden tissue, qualitatively or quantitatively, present in the vagina or peritoneal cavity of said patient.

According to another aspect of the present invention, an in vivo probe includes metal detection means for detecting the presence of ferrous-laden tissues in the vagina or peritoneal cavity of a patient.

According to yet another aspect of the present invention, an apparatus for detecting the presence of endometriosis in a patient includes a probe suitable for in vivo use within the pelvic cavity the patient, detection means for detecting ferrous-laden tissue, the detection means being located within the distal end of the probe and capable of producing a signal when the detection means is in the presence of ferrous-laden tissue; and circuit means operatively connected to the detection means for receiving the signal; and indicator means coupled to the circuit means for indicating the presence of a received signal.

BRIEF DESCRIPTION OF THE DRAWING FIGURES

FIG. 2A is a block diagram schematic of a first alternate embodiment of the apparatus of the present invention.

FIG. 2B is a block diagram schematic of a second alternate embodiment of the apparatus of the present invention.

DETAILED DESCRIPTION OF THE INVENTION

Figure 1A:
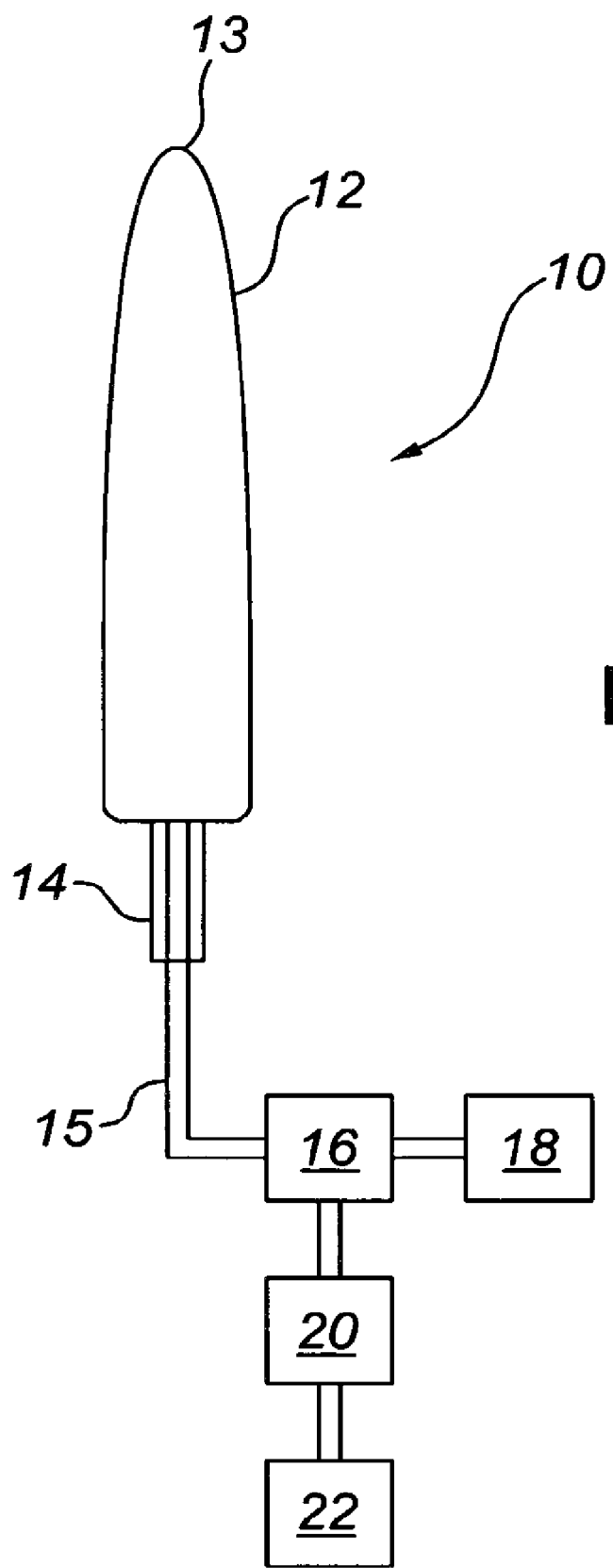
FIG. 1A is a block diagram of the apparatus of the present invention.
Figure 1B:
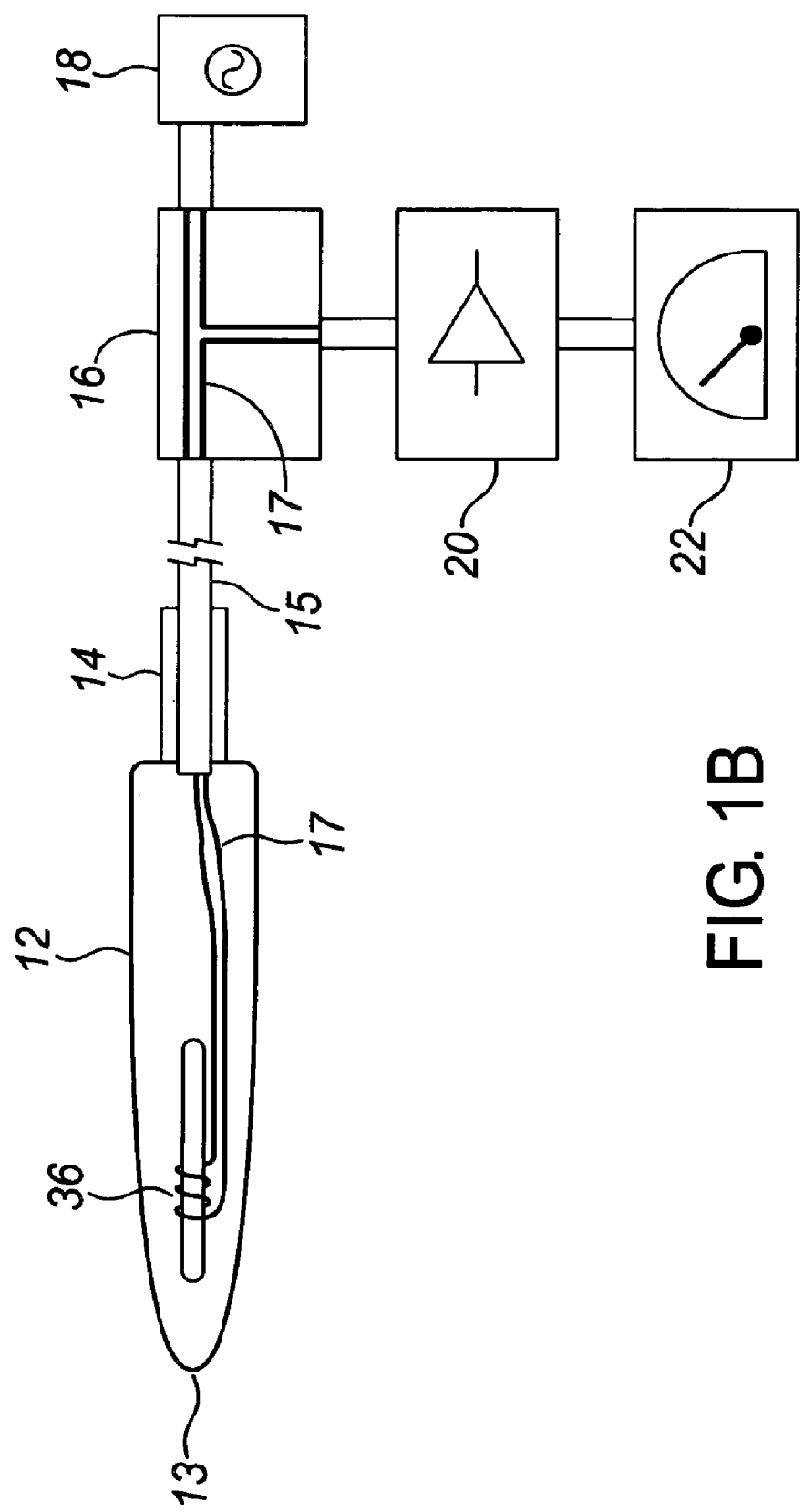
FIG. 1B is a block diagram schematic a first embodiment of the apparatus of the present invention.

The present invention is a method and apparatus for detecting endometriosis. According to FIGS. 1A and 1B, one embodiment of the present invention is shown which comprises of Apparatus 10. Apparatus 10 comprises a probe 12 with handle 14. Probe 12 is connected to balancing unit 16 via cable 15. Bias current for coil 36 is provided by excitation source 18 through balancing unit 16 and wires 17. Balancing unit 16 is also connected to amplifier 20 which, in turn, is connected to indicator 22.

When probe 12 is brought in proximity of metal or ferrous material, such as endometriotic tissue, the current in coil 36 fluctuates due to the presence of metal near coil 36. Amplifier 20 amplifies fluctuations in the current. The amplified fluctuations are then displayed on indicator 22. Indicator 22 may be an analog or digital display giving an indicator of current or voltage as a representation of the bias current fluctuations. Apparatus 10 may be configured to provide qualitative readings whereby the reading indicates the relative amount of ferrous material present compared to a baseline or benchmark reading. Apparatus 10 may also be configured to provide quantitative reading whereby the reading indicates the absolute amount of ferrous material present.

Referring to FIG. 2A, a first alternate embodiment of the apparatus of the present invention is shown. In this embodiment, the detection means is sensor 23 which comprises of a Hall effect sensor. Hall effect sensors, as well known by those skilled in the art, are devices that upon the presence of a magnetic field operate as a solid-state switch. Hall effect devices are non-linear in nature but can be used as measurement devices when their non-linear characteristics are compensated for when analyzing the measurement reading.

Current flowing through coil 36 generates a magnetic field that is detected by sensor 23. Those skilled in the art will appreciated that the placement of sensor 23 and the magnitude of the magnetic field generated by coil 36 will need to be adjusted such that sensor 23 can operate as an effective measurement device suitable for a probe designed for in vivo pelvic examinations.

When probe 12 is used in an in vivo pelvic examination, the presence of ferrous-laden or endometriotic tissues will cause fluctuations in the magnetic field generated by coil 36. These fluctuations are detected by sensor 23 and interpreted by processor 21. A bias current flowing through sensor 23 via wires 19 will be perturbed by the presence of ferrous-laden tissues near sensor 23 in proportion to the amount and proximity of the ferrous-laden tissues and in relation to the non-linear operating characteristics of sensor 23. Processor 21 may include balancing unit 16 and amplifier 20. Processor 21 interprets the fluctuations of the current flowing through sensor 23 to provide a qualitative or quantitative measurement of the ferrous-laden tissues present having regard to the non-linear characteristics of sensor 23.

Processor 21 may be embodied in discrete analog or digital electronic components or in an integrated microcontroller or microprocessor. Processor 21 may further have an analog to digital conversion circuit for converting the analog current measurement from sensor 23 into a digital format that may be interpreted and processed by processor 21. Processor 21 is operatively coupled to display unit 25 that may include indicator 22. Display unit 25 provides the visual indication of the qualitative or quantitative measurement of the ferrous-laden tissues detected during the pelvic exam.

Referring to FIG. 2B, a second alternative embodiment of the apparatus of the present invention is shown. In this embodiment, coil 36 is replaced with permanent magnet 37 within probe 12. Magnet 37 may be any permanent magnet that is suitable for use in an in vivo probe and for working in cooperation with a Hall effect sensor operating as sensor 23.

Figure 3:
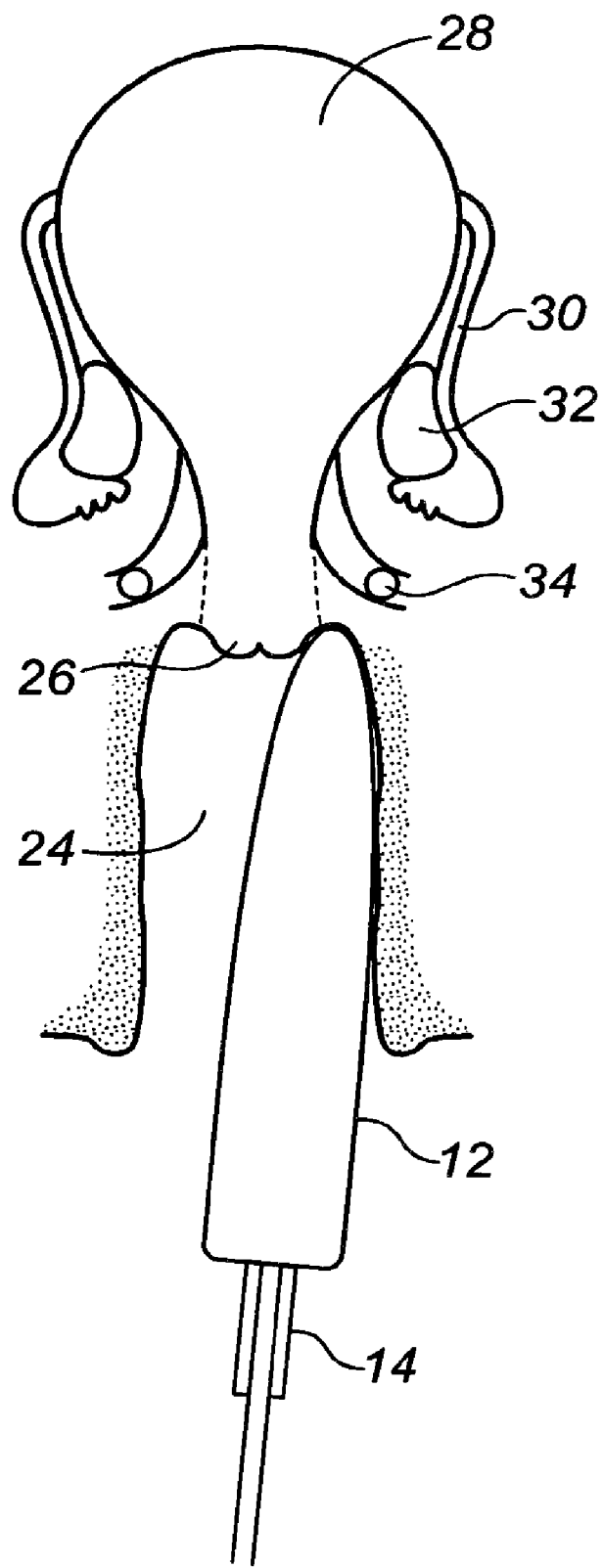
FIG. 3 is a cross-sectional illustration of the apparatus of the present invention being used to detect endometriosis in the vagina of the patient.

Referring to FIG. 3, probe 12 is inserted into vagina 24 of a patient suspected or known to have endometriosis. Probe 12 is constructed to standards suitable for in vivo use as well known to those skilled. Distal end 13 of probe 12 is placed in vagina 24 in areas where presence of endometriosis is suspected. Standard exploration of the pelvic area of the patient is performed to locate cyst 34 with probe 12.

Distal end 13 can be placed 1 to 3 cm away from cyst 34 when probe 12 is placed in vagina 24. The ferromagnetic properties of endometriotic tissues of cyst 34 allow it to be detected by coil 36 located within distal end 13 of probe 12. Use of apparatus 10 in a pelvic exam provides a number of significant indicia. The first of which is the mere presence of iron or ferrous-laden tissues which indicates the presence of endometriosis. The second important indicator is the amount of iron or ferrous-laden tissues that is detected by apparatus 10. The third important indicator is the location reading obtained during the exam which assists in locating iron or ferrous-laden tissues, such as cyst 34.

Repeated use of apparatus 10 as a diagnostic technique in regular pelvic exams assists in early detection of the onset of endometriosis in patients. The method of the present invention is also a useful technique to measure any changes in the location and/or amount of iron or ferrous-laden tissues present in the patient due to endometriosis. This is useful in determining the efficacy of any medical or surgical therapy performed to the patient to treat endometriosis.

Figure 4:
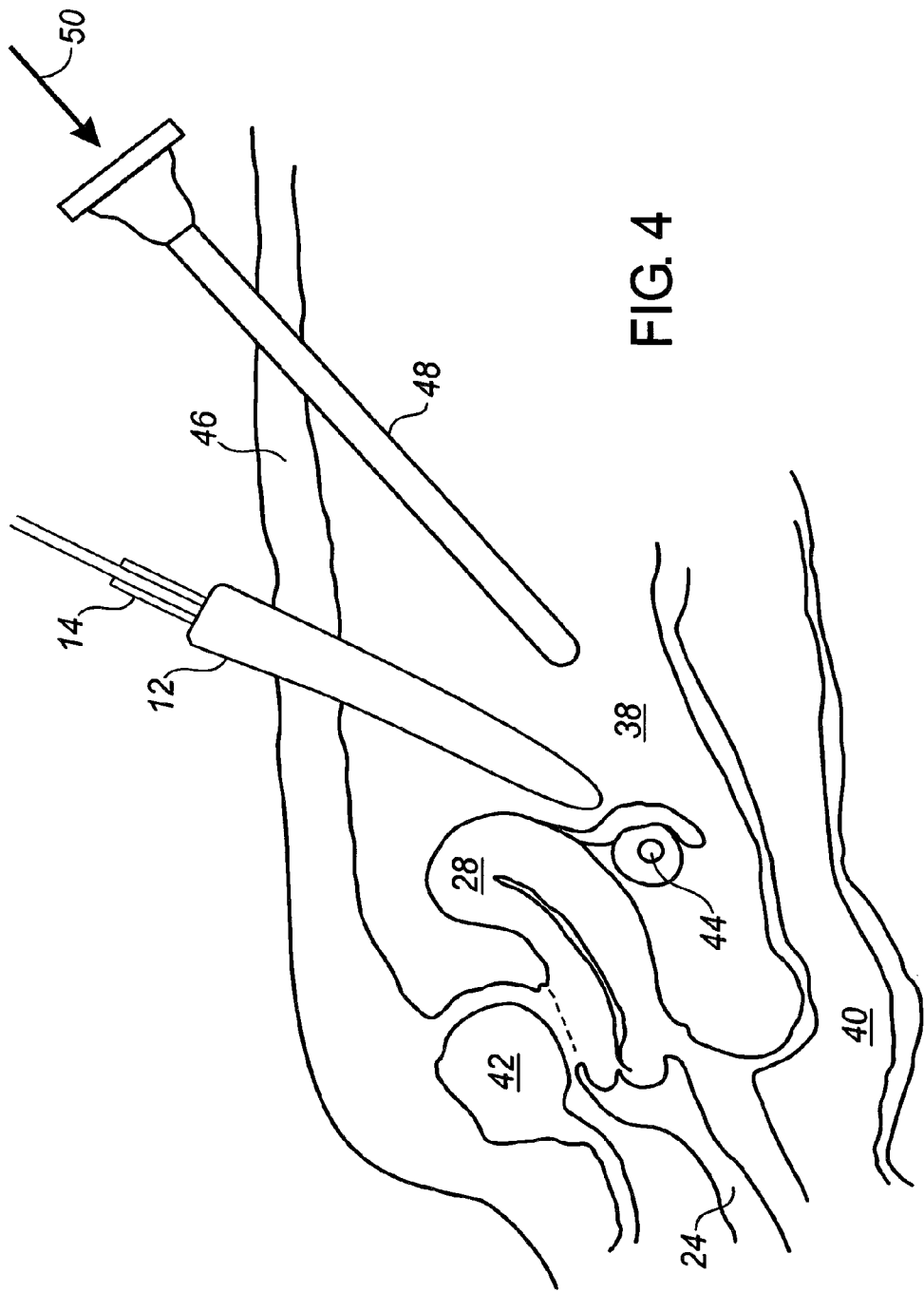
FIG. 4 is a cross-sectional illustration of the apparatus of the present invention being used to detect endometriosis in the peritoneal cavity of the patient.

Referring to FIG. 4, probe 12 may also be used in operative procedures such as laparotomies or laparoscopies. In addition to laparoscope 48, probe 12 is inserted through abdominal wall 46 of the patient into peritoneal cavity 38. Probe 12 is applied to the walls of organs in peritoneal cavity 38, such as uterus 28, bowel 40, bladder 42 and ovary 44, to detect the presence of iron or ferrous-laden tissues. This technique permits the identification or endometriotic tissues when the actual pathology, as viewed through optics 50 of laparoscope 48, is obscured from view due to pathological changes in the pelvic organs.

In addition to the visual indication of the disease, this technique permits the measurement of the extent and/or the amount of iron or ferrous-laden tissues present in the pelvic region of the patient. As mentioned above, these measurements taken from regular pelvic exams can provide early detection of endometriosis in patients. The technique may also be used in combination with the therapeutic treatments to determine the efficacy of such treatments.

Although preferred embodiments have been shown and described, it will be appreciated by those skilled in the art that various changes and modifications can be made without departing from the scope of the invention. The terms and expressions in the preceding specification have been used therein as terms of description and not of limitation, and there is no intention in the use of such terms and expressions of excluding equivalents of the features shown and described or portions thereof, it being recognized that the scope of the invention is defined and limited only by the claims that follow.

I claim:

1. A method for detecting endometriosis, wherein the method comprises the step of placing an in vivo probe in the vagina or peritoneal cavity of a patient to detect the presence of endometriotic tissues, the probe comprising:
    a. a distal end;
    b. magnetic field generating means for generating a magnetic field, the generating means being disposed in the probe;
    c. detection means for detecting a fluctuation of the magnetic field, the detection means being disposed within the distal end of the probe, the detection means configured to produce a signal in response to a fluctuation of the magnetic field when the detection means is proximal to endometriotic tissue;
    d. circuit means coupled to the detection means, the circuit means configured to receive the signal; and
    e. indicator means coupled to the circuit means for indicating the presence of the signal.

2. The method as set forth in claim 1, wherein the probe is configured for detecting endometriotic tissue in the vagina or peritoneal cavity of a patient.

3. The method as set forth in claim 1, wherein the probe is adapted for use during the performance of laparoscopy or laparotomy procedures on a patient.

* * * * *